United States Patent [19]

Hirschberg et al.

[11] Patent Number: 5,397,336
[45] Date of Patent: Mar. 14, 1995

[54] DEFIBRILLATOR/CARDIOVERTER

[75] Inventors: Jakub Hirschberg, Taeby; Martin Obel, Danderyd, both of Sweden

[73] Assignee: Siemens Aktiengesellschaft, Munich, Germany

[21] Appl. No.: 67,946

[22] Filed: May 27, 1993

[30] Foreign Application Priority Data

Jun. 17, 1992 [EP] European Pat. Off. ............ 92110292

[51] Int. Cl.6 ............................................. A61N 1/39
[52] U.S. Cl. ................................................. 607/6; 607/5
[58] Field of Search ............................. 607/5, 6, 7, 8

[56] References Cited

U.S. PATENT DOCUMENTS

| 3,895,639 | 7/1975 | Rodler . | |
|---|---|---|---|
| 4,548,203 | 10/1985 | Tacker, Jr. et al. . | |
| 4,708,145 | 11/1987 | Takcer, Jr. et al. . | |
| 5,088,489 | 2/1992 | Lerman | 607/8 |
| 5,163,427 | 11/1992 | Keimel | 607/5 |
| 5,176,137 | 1/1993 | Erickson et al. | 607/6 |
| 5,275,158 | 1/1994 | Lopin | 607/6 |
| 5,279,291 | 1/1994 | Adams et al. | 607/5 |

FOREIGN PATENT DOCUMENTS

| 0315368 | 5/1989 | European Pat. Off. . |
|---|---|---|
| 0392099 | 10/1990 | European Pat. Off. . |
| 0480569 | 4/1992 | European Pat. Off. . |
| 3919498 | 1/1990 | Germany . |
| 1337824 | 11/1973 | United Kingdom . |
| 2085593 | 4/1982 | United Kingdom . |

OTHER PUBLICATIONS

"Sequential Pulse Defibrillation for Implantable Defibrillators," Bourland et al., Medical Instrumentation, vol. 20, No. 3, May., 1986 (pp. 138–142).

Primary Examiner—William E. Kamm
Assistant Examiner—Scott M. Getzow
Attorney, Agent, or Firm—Hill, Steadman & Simpson

[57] ABSTRACT

In order to be able to set the distribution of current of the defibrillation current across the heart muscle, a defibrillator/cardioverter has n ($n \geq 3$) electrodes connected to a pulse generator having n−1 outputs with a total of n output terminals to which the electrodes are connected. A measuring unit generates a measured signal dependent on the geometrical arrangement of the electrodes with reference to the heart. This measured signal is utilized for setting the pulse heights of the defibrillation pulses to be simultaneously generated at the outputs.

6 Claims, 2 Drawing Sheets

DEFIBRILLATOR/CARDIOVERTER

BACKGROUND OF THE INVENTION

1. Field of the Invention

The present invention relates to a defibrillator/cardioverter of the type having a plurality of n (n≧3) electrodes which are connected to a device for generating electric pulses.

2. Description of the Prior Art

A defibrillator or cardioverter is disclosed in German OS 3,919,498, wherein one of a plurality of electrodes is arranged in the interior of the heart and the remaining electrodes are placed outside of the heart. The external electrodes are electrically connected to one another and are connected to a first of two output terminals of a pulse generator. The electrode arranged in the interior of the heart is connected to the second output terminal. It is thereby achieved that, upon the transmission of an electrical pulse by the pulse generator, the electrical current density is distributed in the heart muscle in accordance with the arrangement of the electrodes and preferably penetrates the thickest zones of the heart muscle, which form the main part of the heart muscle mass, in order to achieve defibrillation or cardioversion. The current distribution, however, can be set only by the arrangement and size of the individual electrodes. The arrangement of the electrodes, and in particular their distance from one another, is limited, however, by the anatomical conditions.

U.S. Pat. No. 4,548,203 discloses a further defibrillator having a plurality of electrodes which are connected in pairs to different outputs of a pulse generator and are placed on different, preferably opposite, sites of the heart. In order to defibrillate the heart, one electric pulse is applied to the individual electrode pairs sequentially via the outputs of the pulse generator, the pulses being separated from one another in each case by a time interval. The spatially and temporally separate pulse transmission is intended to achieve a reduction in the energy required to trigger the defibrillation. In each case, however, only two electrodes simultaneously participate in the pulse transmission, and thus a genuine distribution of the current density to different zones of the heart muscle is difficult to achieve if at all.

In a further defibrillator, disclosed in U.S. Pat. No. 4,708,145, having three electrodes, transmission of defibrillation pulses is performed sequentially between a first electrode and in each case one of the other two electrodes, the pulses again being separated from one another by a time interval.

European Application No. 92104392.3 (corresponding to pending U.S. application Ser. No. 07/856,688, filed Mar. 24, 1992, Hirschberg et al., "Defibrillator/Cardioverter"), discloses an arrangement which achieves a spatially optimum current distribution when the individual electrodes are connected to respective output terminals, which are in turn connected to a plurality of series-connected outputs of a pulse generator which simultaneously transmits an electric pulse at each of those outputs.

SUMMARY OF THE INVENTION

An object of the present invention is to provide a defibrillator or cardioverter with which both a spatially and chronologically optimum current distribution in the heart can be set for achieving optimally effective defibrillation.

This object is inventively achieved in a defibrillator/cardioverter having means for generating the electrical pulses has n−1 outputs connected in series with a total of n output terminals to which the electrodes are connected. The pulse generator simultaneously supplies outputs in the form of an electrical pulse at each of its outputs. Measuring means are connected to the electrodes for acquiring an electrical measured quantity dependent on the arrangement of the electrodes with reference to the heart tissue, with signal corresponding to the measured quantity being supplied to means for individually setting the pulse heights of the pulses at the outputs of the pulse generator dependent on the acquired measured quantity. During defibrillation or cardioversion of the heart, the current distribution across the heart muscle tissue is thereby adjustable via the pulse heights (amplitudes), i.e. electrical voltages at the outputs of the pulse generator so that the respective arrangement of the electrodes with reference to the heart and the geometrical distribution of the heart tissue between the electrodes are taken into consideration in the adjustment of the current distribution.

According to a preferred embodiment of the defibrillator/cardioverter of the invention, the measuring means is an impedance measuring device for measuring the electrical impedance between the electrodes. The measured impedance value that is thus obtained provides reliable information about the spatial distribution of the heart muscle mass with reference to the arrangement of the electrodes, so that an optimum setting of the pulse heights of the pulses is possible for achieving a prescribed defibrillation current density in the heart muscle.

In an alternative version of the measuring device, at least one current measuring means is arranged between one of the output terminals of the pulse generator and the electrode connected thereto, whereby the pulse generator generates a test pulse at least one of its outputs in order to acquire the measured quantity. Conclusions about the spatial distribution of the heart muscle mass between the electrodes can thereby be drawn from the flow of current produced by the test pulse.

In order to be able to pre-program the pulse heights at the outputs of the pulse generator for a desired distribution of current in the heart, particularly given a fashioning of the defibrillator/cardioverter of the invention as an implantable device, the means for setting the pulse heights are connected to a parameter memory wherein parameter values for the pulse heights are stored, and that the parameter memory is connected to a telemetry means for the transmission of the parameter values between the parameter memory and a programming device. The measured values supplied by the measuring device, for example, can be displayed on a display of the programming device and provide the operator with promptings to program the individual parameter values for the pulse heights in order to achieve the desired distribution of current in the heart.

In another embodiment of the defibrillator/cardioverter of the invention, the pulse generator includes n−1 capacitors connected in series that can be connected to a charging circuit via a switch arrangement for charging to different, prescribed charging voltages. Further, the terminal points of the individual capacitors are connected via controllable switches to the output terminals of the pulse generator. As long as the switch arrangement is closed, the capacitors are charged to the respective charging voltages, by either simultaneously connecting the capacitors to respective voltage outputs of the charging circuit allocated to the capacitors or by successively individually connecting the capacitors to a single voltage output of the charging circuit. The pulse output to the electrodes subsequently ensues with a simultaneous closing of the controllable switches.

In order to be able to additionally influence the courses of current over the individual electrodes, passive electrical components, preferably inductances and/or resistors are preferably inserted into the lines between the output terminals of the pulse generator and the electrodes. A limitation of current is thus achieved in case of a short-circuit between the electrodes. Moreover, curves of current can be achieved that deviate from an exponentially decaying curve of the type that occurs given a simple capacitor discharge and, for example, can have the form of a highly attenuated sine oscillation; such a pulse shape has proven especially effective for defibrillation purposes.

DESCRIPTION OF THE PREFERRED EMBODIMENTS

Figure 1:
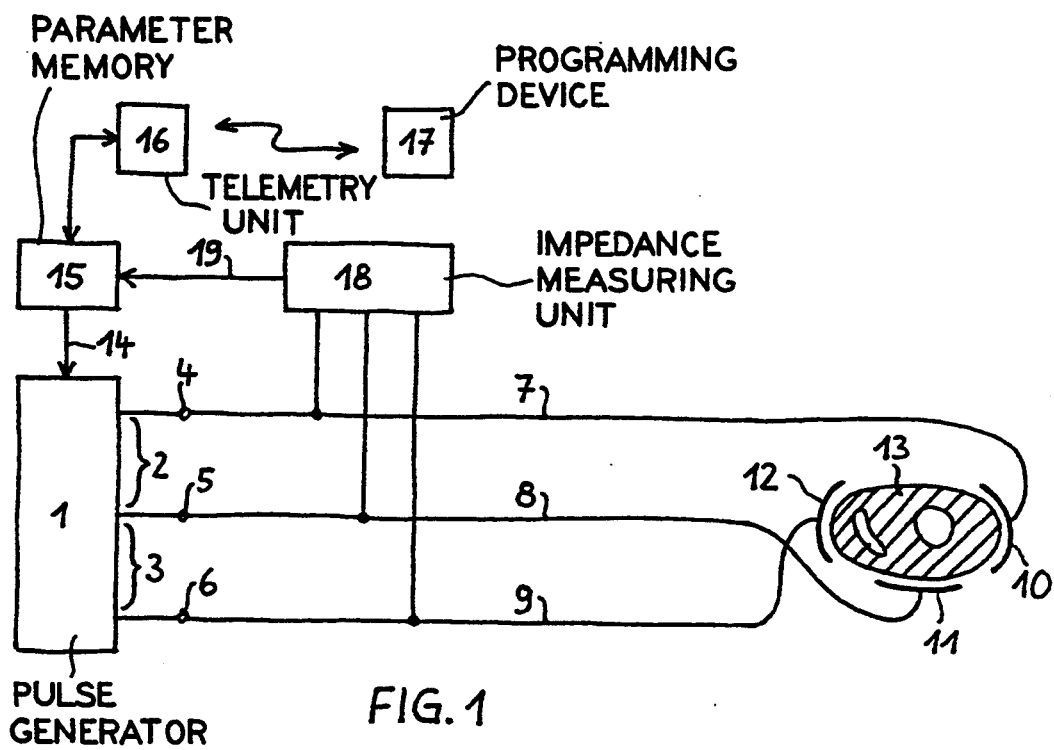
FIG. 1 is a schematic block diagram of a first exemplary embodiment of the defibrillator/cardioverter of the invention having an impedance measuring means.

In the block circuit diagram of an implantable defibrillator or cardioverter shown in FIG. 1, a pulse generator 1 has two series-connected outputs 2 and 3 with a total of three output terminals 4, 5 and 6 which are connected via electrode leads 7, 8 and 9 to three electrodes 10, 11 and 12 that are arranged at a heart 13 (shown in cross section). The illustrated arrangement of the electrodes 10, 11 and 12 with reference to the heart 13 is to be understood as only one of many examples. For example, the electrodes 10, 11 and 12 can also be arranged in the vena cava, in the right ventricle, as well as subcutaneously, lying opposite the left ventricle of the heart.

The pulse generator 1 is connected via a control line 14 to a parameter memory 15 wherein different values for the pulse heights of the pulses to be generated at the outputs 1 and 3 are stored. These values can be transmitted between the parameter memory 15 and an external programming device 17 by a telemetry unit 16 that is connected to the parameter memory 15. An impedance measuring unit 18 is connected to the output terminals 4, 5 and 6. The impedance measuring unit 18 measures the electrical impedance of the heart tissue 13 between the electrodes 10, 11 and 12 at prescribed points in time. The measured impedance is evaluated in such a way in the impedance measuring unit 18 that information about the spatial arrangement of the electrodes 10, 11 and 12 with respect to the heart 13 and about the distribution of the heart muscle mass 13 between the electrodes 10, 11 and 12 are obtained. As FIG. 1 shows, the heart muscle mass is very irregularly distributed over the cross section of the heart 13. Moreover, the electrodes 10, 11 and 12—as already set forth above—, can be arranged at very different positions with reference to the heart 13.

These relationships can be mensurationally acquired in a simple way by impedance measurement between the three electrodes 10, 11 and 12. The measured impedance signal evaluated in this way is supplied to the parameter memory 15 via a control line 19. Either an automatic matching of the programmed values for the pulse heights of the pulses to be generated to the measured impedance signals ensues in the parameter memory 15, or the measured impedance signal is transmitted via the telemetry unit 15 to the programming device 17 and is displayed in order to provide the operator with additional information for the programming of the pulse heights. Additionally, the operator can program boundary conditions for the automatic setting of the pulse height by the measuring device 18.

For defibrillation of the heart 13, defibrillation pulses, with respective pulse heights set such that a desired current distribution is achieved in the heart 13, are simultaneously generated at the outputs 2 and 3 of the pulse generator 1. The influence of the heart geometry and the arrangement of the electrodes 10, 11 and 12 on the distribution of current have thereby been taken into consideration in setting the pulse heights by the preceding impedance measurement and corresponding adaptation of the pulse heights.

Figure 2:
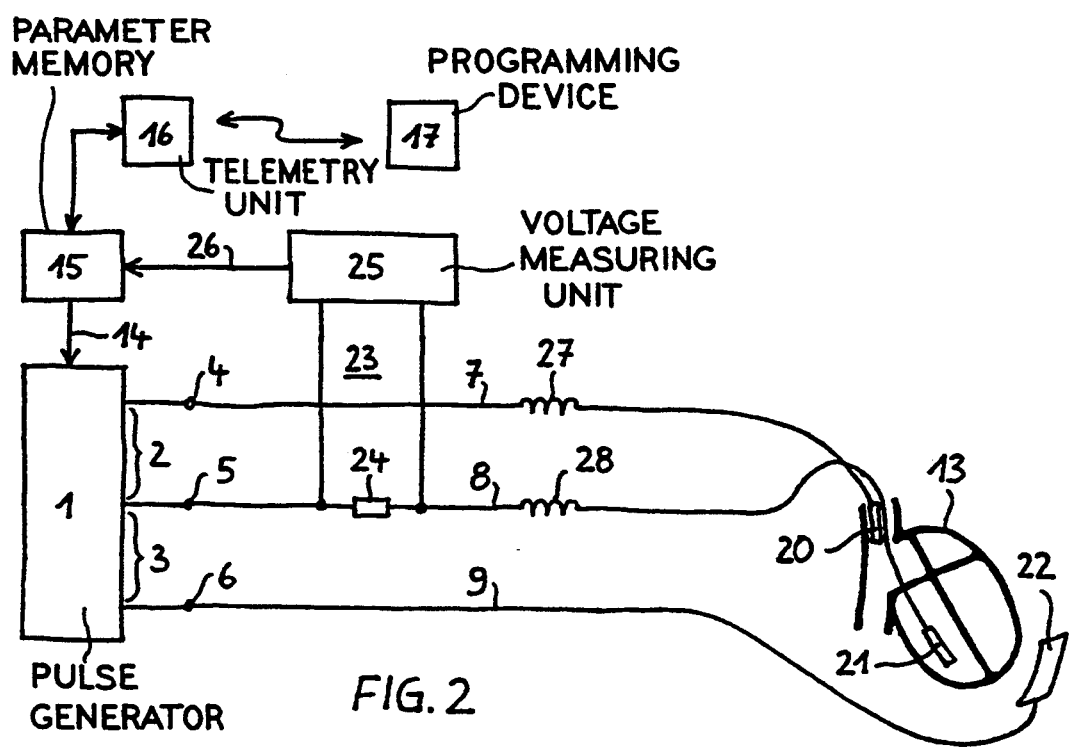
FIG. 2 is a schematic block diagram of a further exemplary embodiment having a current measuring means.

FIG. 2 shows another exemplary embodiment of the defibrillator/cardioverter of the invention, whereby, just as shown in FIG. 1, a pulse generator 1 has two series-connected outputs 2 and 3 having the total of three output terminals 4, 5 and 6 connected via electrode leads 7, 8 and 9 to electrodes 20, 21 and 22 arranged in the region of the heart 13. A current measuring unit 23, composed of a precision resistor 24 and a voltage measuring unit 25 arranged parallel thereto, is arranged between the output terminal 5 and the electrode 21 connected thereto. The current measuring unit 23 or voltage measuring unit 25 has an output side connected via a control line 26 to a parameter memory 15 in which parameter values for setting the pulse heights at the outputs 2 and 3 of the pulse-generating means 1 are stored. To that end, the parameter memory 15 is connected via a control line 14 to the pulse generator 1, and also communicates with a programming device 17 via a telemetry unit 16. Two inductances 27 and 28 that serve the purpose of shaping the current pulse and limiting the short-circuit current are arranged in the electrode leads 7 and 8.

In order to obtain information about the arrangement of the electrodes 20, 21 and 22 and about the spatial distribution of the heart muscle mass between the electrodes 20, 21 and 22, the pulse generator 1 simultaneously generates respective test pulses at its outputs 2 and 3 that have a defined pulse height that lies far below the defibrillation threshold of the heart 13. The course of the current in the electrode lead 8 resulting therefrom is dependent on the electrode configuration with reference to the heart 13, and as set forth with reference to the exemplary embodiment of FIG. 1, is utilized for setting or correcting the pulse height of the pulses to be generated at the outputs 2 and 3.

Figure 3:
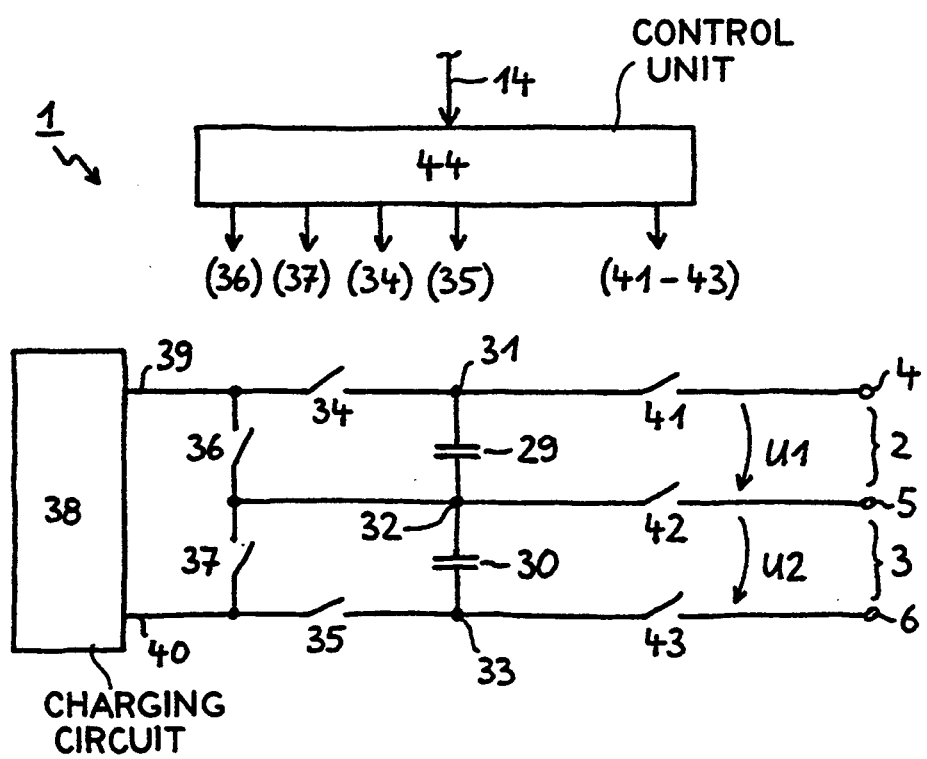
FIG. 3 is a schematic block diagram of an exemplary embodiment of the pulse generator in FIGS. 1 and 2.

FIG. 3 shows an exemplary embodiment of the pulse generator 1 including two series-connected capacitors 29 and 30 that have their terminals 31, 32 and 33 connected to a charging circuit 38 via a controllable switch arrangement composed of four individually controllable switches 34, 35, 36 and 37. The two switches 34 and 35 respectively connect the outer terminals 31 and 33 of the series circuit of the capacitors 29 and 30 to the two output terminals 39 and 40 of the voltage output of the charging circuit 38, whereas the switches 36 and 37 connect the middle terminal 32 to the two output terminals 39 and 40. The terminals 31, 32 and 33 of the capacitors 29 and 30, moreover, are respectively connected via three simultaneously controllable switches 41, 42 and 43 to the output terminals 4, 5 and 6 of the pulse generator 1. The controllable switches 34 through 37 and 41 through 43 are controlled by a control unit 44. The control unit 44 is in turn controlled by the parameter memory via the control line 14 (FIGS. 1, 2).

In order to charge the capacitor 29 to a first voltage U1 and the capacitor 30 to a second voltage U2, the switches 34 and 37 are first closed until the capacitor 29 has charged to the voltage U1. Subsequently, given opened switches 34 and 37, the switches 35 and 36 are closed; when the voltage at the capacitor 30 reaches the value U2, then the switches 35 and 36 are opened. For pulse output with the voltage U1 at the output 2 and the voltage U2 at the output 3, the switches 41, 42 and 43 are closed.

Although modifications and changes may be suggested by those skilled in the art, it is the intention of the inventors to embody within the patent warranted hereon all changes and modifications as reasonably and properly come within the scope of their contribution to the art.

We claim as our invention:

1. A defibrillator/cardioverter comprising:
    a plurality of n electrodes, n being greater than or equal to three, adapted for arrangement relative to the heart of a patient with heart tissue between said electrodes for delivering electrical pulses having a pulse height to said heart;
    pulse generator means including means for establishing n−1 series-connected circuits having a total of n output terminals respectively connected to said n electrodes, for generating said electrical pulses simultaneously and respectively in said output circuits;
    means for measuring an electrical quantity which is dependent on said arrangement of said electrodes and said heart tissue between said electrodes, and for generating an electrical signal corresponding to the measured electrical quantity; and
    control means, supplied with said electrical signal from said means for measuring, for controlling said pulse generator means for individually setting the respective pulse heights of said electrical pulses in said output circuits of said pulse generator means dependent on said measured electrical quantity.

2. A defibrillator/cardioverter as claimed in claim 1 wherein said means for measuring an electrical quantity comprises means for measuring the electrical impedance between said electrodes.

3. A defibrillator/cardioverter as claimed in claim 1 wherein said means for measuring an electrical quantity comprises current measuring means connected between one of said output terminals and the electrode connected to that output terminal, and wherein said pulse generator means includes means for generating a test pulse at said one of said output terminals for acquiring a measurement of current.

4. A defibrillator/cardioverter as claimed in claim 1 further comprising:
    a parameter memory, connected to said control means, in which a plurality of parameter values for different pulse heights are stored; and
    telemetry means for telemetrically communicating with said parameter memory for telemetrically transmitting said parameter values between said parameter memory and a remote location.

5. A defibrillator/cardioverter as claimed in claim 1 wherein said pulse generator means comprises:
    n-1 series-connected capacitors;
    a charging circuit for charging said capacitors;
    a first set of switches respectively connected between said charging circuit and said capacitors and operable by said control means for respectively charging said capacitors to different, prescribed charging voltages; and
    a second set of switches respectively connected between said capacitors and said output terminals also operated by said control means for selectively connecting said capacitors to said electrodes.

6. A defibrillator/cardioverter as claimed in claim 1 further comprising at least one passive electrical component connected between at least one of said output terminals and the electrode connected to said at least one of said output terminals.

* * * * *